United States Patent
Matsuda

(10) Patent No.: US 9,918,689 B2
(45) Date of Patent: Mar. 20, 2018

(54) MEDICAL IMAGE PROCESSING APPARATUS AND X-RAY CT APPARATUS

(71) Applicant: TOSHIBA MEDICAL SYSTEMS CORPORATION, Otawara-Shi (JP)

(72) Inventor: Keiji Matsuda, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 324 days.

(21) Appl. No.: 14/800,357

(22) Filed: Jul. 15, 2015

(65) Prior Publication Data
US 2015/0313565 A1 Nov. 5, 2015

Related U.S. Application Data

(63) Continuation of application No. PCT/JP2014/051801, filed on Jan. 28, 2014.

(30) Foreign Application Priority Data

Jan. 29, 2013 (JP) .................................. 2013-014752
Jan. 28, 2014 (JP) .................................. 2014-013152

(51) Int. Cl.
*A61B 6/00* (2006.01)
*A61B 6/03* (2006.01)

(52) U.S. Cl.
CPC ............ *A61B 6/5205* (2013.01); *A61B 6/032* (2013.01); *A61B 6/4233* (2013.01); *A61B 6/585* (2013.01); *A61B 6/586* (2013.01); *A61B 6/54* (2013.01)

(58) Field of Classification Search
None
See application file for complete search history.

(56) References Cited

U.S. PATENT DOCUMENTS

2008/0240357 A1* 10/2008 Jabri .................... A61B 6/4035
378/101

FOREIGN PATENT DOCUMENTS

JP  62-227323 A  10/1987
JP  03-090136 A  4/1991
(Continued)

OTHER PUBLICATIONS

International Search Report dated Apr. 8, 2014 for PCT/JP2014/051801 filed Jan. 28, 2014 with English Translation.

(Continued)

*Primary Examiner* — Hoon Song
(74) *Attorney, Agent, or Firm* — Oblon, McClelland, Maier & Neustadt, L.L.P.

(57) ABSTRACT

According to one embodiment, a medical image processing apparatus includes a storage circuit and processing circuitry. The storage circuit stores correction data for emergency and/or correction data for normal time. The processing circuitry outputs a command to perform imaging of a patient and acquire radiographic data, and determines whether imaging time of the patient is in a first period during which temperature of an X-ray detector is stable or in a second period during which the temperature is not stable, before the imaging of the patient. In addition, the processing circuitry corrects the radiographic data by using the correction data for emergency when the imaging time is in the second period, and corrects the radiographic data by using the correction data for normal time when the imaging time is in the first period.

10 Claims, 3 Drawing Sheets

(56) References Cited

FOREIGN PATENT DOCUMENTS

| JP | 06-066635 U | 9/1994 |
|---|---|---|
| JP | 2002-085391 A | 3/2002 |
| JP | 2005-111193 A | 4/2005 |
| JP | 2007-135749 A | 6/2007 |
| JP | 2007-185375 A | 7/2007 |
| JP | 2010-269083 A | 12/2010 |
| JP | 2011-167423 A | 9/2011 |
| JP | 2012-210291 A | 11/2012 |
| JP | 2013-013442 A | 1/2013 |
| WO | WO 2010/122609 A1 | 10/2010 |

OTHER PUBLICATIONS

English language translation of International Preliminary Report on Patentability and Written Opinion dated Aug. 4, 2015 in PCT/JP2014/051801.

Japanese Office Action dated Sep. 26, 2017 in Japanese Patent Application No. 2014-013152.

* cited by examiner

MEDICAL IMAGE PROCESSING APPARATUS AND X-RAY CT APPARATUS

CROSS-REFERENCE TO RELATED APPLICATIONS

This application is a Continuation Application of No. PCT/JP2014/51801, filed on Jan. 28, 2014, and the PCT application is based upon and claims the benefit of priority from Japanese Patent Application No. 2013-14752, filed on Jan. 29, 2013, and Japanese Patent Application No. 2014-13152, filed on Jan. 28, 2014, the entire contents of which are incorporated herein by reference.

FIELD

Embodiments described herein relate generally to a medical image processing apparatus and an X-ray CT apparatus.

BACKGROUND

In an X-ray CT apparatus, it is known that sensitivity change of an X-ray detector due to its temperature influences projection data. Specifically, because sensitivity of an X-ray detector changes depending on its temperature, an X-ray CT apparatus is configured to image an object at a stable state of temperature of its X-ray detector and to correct projection data of the imaged object by using preliminarily prepared correction data.

Therefore, when imaging of an object is performed with an X-ray CT apparatus, temperature of its X-ray detector is stabilized by carrying a current from two to four hours before start time of imaging in order to stabilize the temperature state of the X-ray detector.

Here, depending on the hospitals, energization is performed from several hours before start of imaging by using a timer in many cases. Moreover, an X-ray CT apparatus is used by energizing the X-ray detector consecutively for twenty-four hours in designated emergency hospitals, emergency lifesaving centers, etc. in many cases.

Meanwhile, as to methods of generating the correction data used for correcting sensitivity of X-ray data, technology related to a correction data generating method, in which correction data based on phantom data are generated at a predetermined base time point and new correction data are generated so as to reflect temporal change on the previously generated correction data, is disclosed (see Japanese Patent Application Laid-open Publication No. 2007-135749, for example).

Incidentally, hospitals, which have selected to perform energization by using a timer, cannot deal with unscheduled examination such as emergency cases, and thus such hospitals are unavoidably constrained to change their system to energize the X-ray detector consecutively for twenty-four hours in many cases. On the other hand, there have been many demands that power supply to the X-ray detector should be stopped during nighttime and the X-ray detector should be energized only during imaging in terms of saving power.

Here, as a case where the X-ray detector influences projection data, it is known that artifact such as a ring etc. occurs if radiographic data obtained by imaging are corrected with the use of correction data preliminarily prepared at an unstable state of temperature of the X-ray detector.

Therefore, under the state where the temperature of the X-ray detector is not stable, satisfactory projection data can be obtained by the following two steps. The first step is to generate correction data in accordance with temperature state of the X-ray detector, and the second step is to correct the radiographic data obtained through imaging at the time of the first step by using the correction data generated in accordance with the temperature state of the X-ray detector.

However, the temperature of the X-ray detector rises in accordance with elapsed time after start of imaging of an object. Thus, accurate correction cannot be performed by correcting radiographic data with the use of the generated correction data. In addition, because setting conditions of the generated correction data are different from the latest conditions as the temperature of the X-ray detector becomes more stable, artifact occurs in the result even if the radiographic data are corrected by the generated correction data.

DETAILED DESCRIPTION

Figure 1:
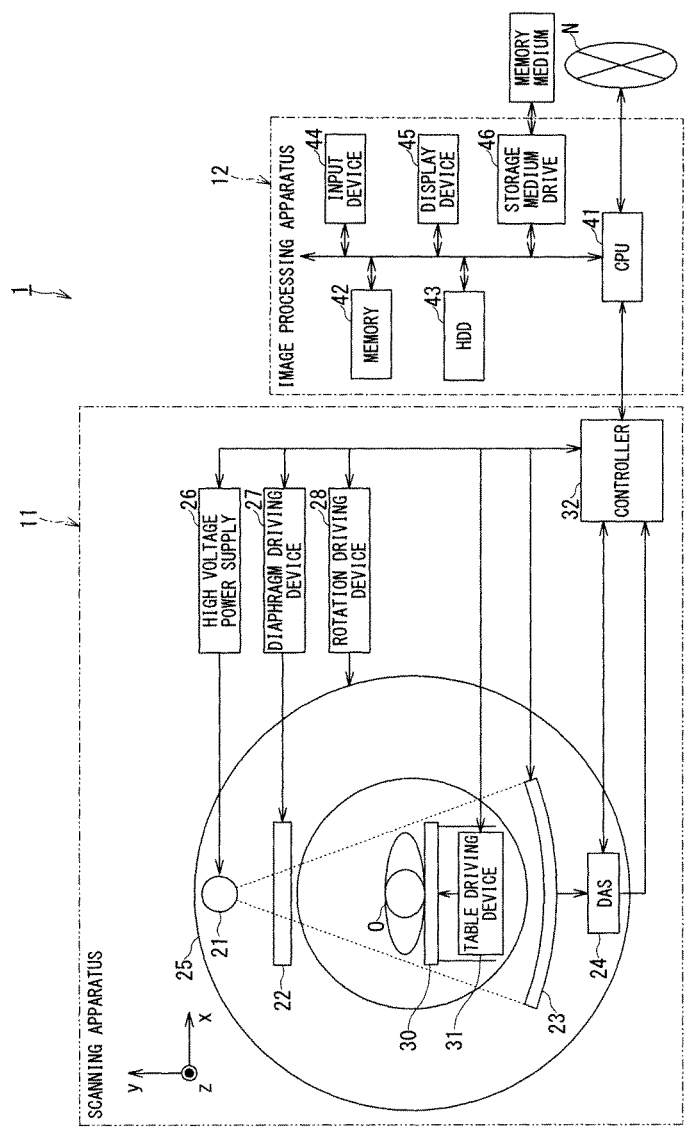
FIG. 1 is a configuration diagram showing the X-ray CT apparatus of the present embodiment.

A medical image processing apparatus and an X-ray CT apparatus according to the present embodiment will be described with reference to the accompanying drawings.

In order to achieve the above-mentioned assignment, the medical image processing apparatus of the present embodiment includes a storage circuit configured to store correction data for emergency and/or correction data for normal time; and processing circuitry configured to (a) output a command to perform imaging of a patient and acquire radiographic data, (b) determine whether imaging time of the patient is in a first period during which temperature of an X-ray detector is stable or in a second period during which the temperature is not stable, before the imaging of the patient, and (c) correct the radiographic data by using the correction data for emergency when the imaging time is in the second period, and correct the radiographic data by using the correction data for normal time when the imaging time is in the first period.

In order to achieve the above-mentioned assignment, the X-ray CT apparatus of the present embodiment includes an X-ray source configured to irradiate X-rays; an X-ray detector configured to detect X-rays penetrating a patient; a data acquisition circuit configured to acquire radiographic data of X-rays detected by the X-ray detector; a storage circuit configured to store correction data for emergency and/or correction data for normal time; and processing circuitry configured to (a) output a command to acquire radiographic data by performing imaging of the patient using the X-ray source, the X-ray detector, and the data acquisition circuit, (b) determine whether imaging time of the patient is in a first period during which temperature of the X-ray detector is stable or in a second period during which the temperature is not stable, before the imaging of the patient, (c) correct the radiographic data by using the correction data for emergency when the imaging time is in the second period, and correct the radiographic data by using the correction data for normal time when the imaging time is in the first period, and (d) reconstruct an X-ray CT image by using corrected radiographic data.

Although an example in which the technology of the present embodiment is applied to an X-ray CT apparatus will be explained below, the technology of the present embodiment is applicable to a single image processing apparatus (medical image processing apparatus).

In addition, there are various types of X-ray CT apparatuses in the present embodiment. One of them is a rotate/rotate type in which an X-ray source and an X-ray detector integrally rotate around an object. Another of them is a stationary/rotate type in which multiple detecting elements are arrayed in a ring-like state and only the X-ray source rotates around an object. The technology of the present invention can be applied to any type of X-ray CT apparatuses. As an example here, it is explained as the currently mainly used rotate/rotate type.

In addition, as to mechanism of converting incident X-rays into electric charges, an indirect conversion type and a direct conversion type are the main types. In the indirect conversion type, X-rays are converted into light with the use of fluorescent body such as scintillator etc. and then the light is converted into electric charges with the use of a photoelectric conversion element such as a photodiode etc. In the direct conversion type, a photoconductive phenomenon (i.e. generation of electron-hole pairs inside semiconductor caused by X-rays and transfer of the electron-hole pairs to an electrode) is used.

Moreover, in recent years, productization of a so-called multi-tube type X-ray CT apparatus in which plural pairs of X-ray sources and X-ray detectors are mounted on a rotating ring has been promoted, and development of its peripheral technology has been promoted. The X-ray CT apparatus of the present embodiment can be applied to any of a conventional single-tube type X-ray CT apparatus and a multi-tube type X-ray CT apparatus. As an example here, it is explained as a single-tube type X-ray CT apparatus.

FIG. 1 is a configuration diagram showing the X-ray CT apparatus 1 of the present embodiment.

In FIG. 1, the X-ray CT apparatus 1 of the present embodiment, which performs injection of a contrast agent to an object and a scan of the object, is shown. As shown in FIG. 1, the X-ray CT apparatus 1 is roughly composed of a scanning apparatus 11 and an image processing apparatus (medical image processing apparatus) 12.

The scanning apparatus 11 of the X-ray CT apparatus 1 is normally installed in an examination room and is configured to generate X-ray transmission data of an object (patient) O.

The image processing apparatus 12 is normally installed in a control room adjacent to the examination room, and the image processing apparatus 12 is configured to generate projection data based on the transmission data and perform generation and display of reconstructed images.

The scanning apparatus 11 of the X-ray CT apparatus 1 includes an X-ray tube (X-ray source) 21, a diaphragm 22, an X-ray detector 23, a DAS (Data Acquisition System) 24, a rotary unit 25, a high voltage power supply 26, a diaphragm driving device 27, a rotation driving device 28, a table 30, a table driving device 31, and a controller 32.

The X-ray tube 21 generates X-rays by making an electron beam collide against a metal target in accordance with a tube voltage supplied from the high voltage power supply 26, and irradiates the generated X-rays toward the X-ray detector 23. Fan beam X-rays or cone beam X-rays are generated by the X-rays irradiated from the X-ray tube 21. Electric power necessary for irradiating X-rays is supplied to the X-ray tube 21, under the control of the controller 32 via the high voltage power supply 26.

The diaphragm 22 adjusts the irradiation range of X-rays irradiated from the X-ray tube 21 in the slice direction by using the diaphragm driving device 27. In other words, the irradiation range of X-rays can be adjusted in the slice direction by changing an aperture of the diaphragm 22 with the use of the diaphragm driving device 27.

The X-ray detector 23 is a one-dimensional array-type detector (also referred to as a single slice type detector) which includes a plurality of detecting elements in a channel direction and one detecting element in a column (slice) direction. Alternatively, the X-ray detector 23 is a two-dimensional array-type detector (also referred to as a multi-slice type detector) which includes X-ray detecting elements arrayed in a matrix (i.e. a plurality of X-ray detecting elements are arrayed in the channel direction and plural columns of X-ray detecting elements are arrayed in the slice direction). Each of the X-ray detecting elements of the X-ray detector 23 detects X-rays irradiated from the X-ray tube 21. Incidentally, in the present embodiment, a non-illustrated temperature sensor is installed in the X-ray detector 23, and the X-ray CT apparatus is configured to be able to detect the temperature of the X-ray detector 23.

The DAS 24 amplifies signals of the transmission data detected by the respective X-ray detecting elements of the X-ray detector 23 and converts the amplified signals into digital signals. These data outputted from the DAS 24 are inputted to the image processing apparatus 12 via the controller 32 of the scanning apparatus 11. Incidentally, the data outputted at this timing are referred to as radiographic data. In addition, when the temperature information indicating the temperature of the X-ray detector 23 is acquired in the X-ray detector 23, the DAS 24 transmits temperature information indicating the temperature of the X-ray detector 23 to the image processing apparatus 12 via the controller 32 of the scanning apparatus 11.

The rotary unit 25 integrally supports the X-ray tube 21, the diaphragm 22, the X-ray detector 23, and the DAS 24. The rotary unit 25 is configured to be able to integrally rotate the X-ray tube 21, the diaphragm 22, the X-ray detector 23, and the DAS 24 around the object O, under the state where the X-ray tube 21 and the X-ray detector 23 face each other. Incidentally, the direction in parallel with the rotary center axis of the rotary unit 25 is defined as a Z axis direction, and a plane orthogonal to this Z axis is defined by using an X axis direction and a Y axis direction.

The high voltage power supply 26 supplies electric power necessary for irradiating X-rays to the X-ray tube 21, under the control of the controller 32.

The diaphragm driving device 27 has a structure of adjusting the X-ray irradiation range in the slice direction by controlling the diaphragm 22 under the control of the controller 32.

The rotation driving device 28 has a structure of rotating the rotary unit 25 around its cavity region under the control of the controller 32, under the state where the rotary unit 25 maintains its positional relationship.

The table 30 is configured to be able to load the object O thereon.

The table driving device 31 has a structure of moving the table 30 upward and downward along the Y axis direction and inserting/retracting the table 30 along the Z axis direction under the control of the controller 32. The center part of the rotary unit 25 is open, and the object O loaded on the table 30 placed at this opened part is inserted.

The controller 32 is composed of a CPU (Central Processing Unit) and a memory. The controller 32 makes the X-ray CT apparatus 1 perform a scan by controlling the X-ray detector 23, the DAS 24, the high voltage power supply 26, the diaphragm driving device 27, the rotation driving device 28, the table driving device 31, etc.

The image processing apparatus 12 of the X-ray CT apparatus 1 is configured on the basis of a computer and can intercommunicate with a network N such as a LAN (Local Area Network) of a medical institution etc.

The image processing apparatus 12 is roughly composed of basic hardware such as a CPU 41, a memory 42, a HDD (Hard Disc Drive) 43, an input device 44, a display device 45, etc. The CPU 41 is interconnected with the respective hardware components of the image processing apparatus 12 via a bus as a common signal transmission channel. Incidentally, the image processing apparatus 12 sometimes includes a storage medium drive 46.

The CPU 41 is a control device having configuration of an integrated circuit (Large-Scale Integration) whose electronic circuits composed of semiconductor are sealed in a package with a plurality of terminals. When the input device 44 is manipulated by an operator such as a doctor etc. to input a command, the CPU 41 performs a program stored in the memory 42. Alternatively, the CPU 41 loads (a) a program stored in the HDD 43, (b) a program transferred from the network N and installed in the HDD 43, or (c) a program read out from a storage medium mounted on the storage medium drive 46 and installed in the HDD 43, into the memory 42, and performs the loaded program.

The memory 42 is a memory device configured of components such as a ROM (Read Only Memory), a RAM (Random Access Memory) and so on. The memory 42 stores IPL (Initial Program Loader), BIOS (Basic Input/Output System) and data, and the memory 42 is used for temporary storage of data and a work memory of the CPU 41.

The HDD 43 is a memory device constituted with an undetachable built-in metal disk on which magnetic substance is coated or evaporated. The HDD 43 is a memory device which stores programs (including application programs, an OS (Operating System), etc.) installed in the image processing apparatus 12 and data such as projection data, image data, etc. In addition, graphics can be frequently used in the OS for displaying information for an operator, so that the X-ray CT apparatus 1 can provide GUI (Graphical User Interface) by which basic operation is enabled by manipulating the input device 44.

The input device 44 is a pointing device which an operator can manipulate, and an input signal in accordance with manipulation on the input device 44 is transmitted to the CPU 41.

The display device 45 includes a non-illustrated image composition circuit, a VRAM (Video Random Access Memory), a monitor, and so on. The image composition circuit generates composed data in which text data of various parameters etc. are composed with image data. The VRAM expands the composed data as data displayed on a monitor. The monitor is configured of a liquid crystal display, CRT (Cathode Ray Tube), etc. and sequentially displays the expanded data.

The storage medium drive 46 is configured so that a memory medium can be detachably mounted thereon. The storage medium drive 46 reads out data (including programs) stored in the mounted memory medium, outputs the data, and write the data provided via a bus onto the mounted memory medium. Such a memory medium can be provided as so-called package software.

The image processing apparatus 12 generates projection data by performing correction processing (preprocessing) such as logarithmic transformation processing, sensitivity correction processing, etc. on the radiographic data supplied from the DAS 24 of the scanning apparatus 11. In addition, the image processing apparatus 12 performs, for example, various types of correction processing such as processing of eliminating scattering rays etc. on the generated projection data. The image processing apparatus 12 generates image data by reconstructing the corrected projection data, and stores the image data after performing various types of image processing on them.

Figure 2:
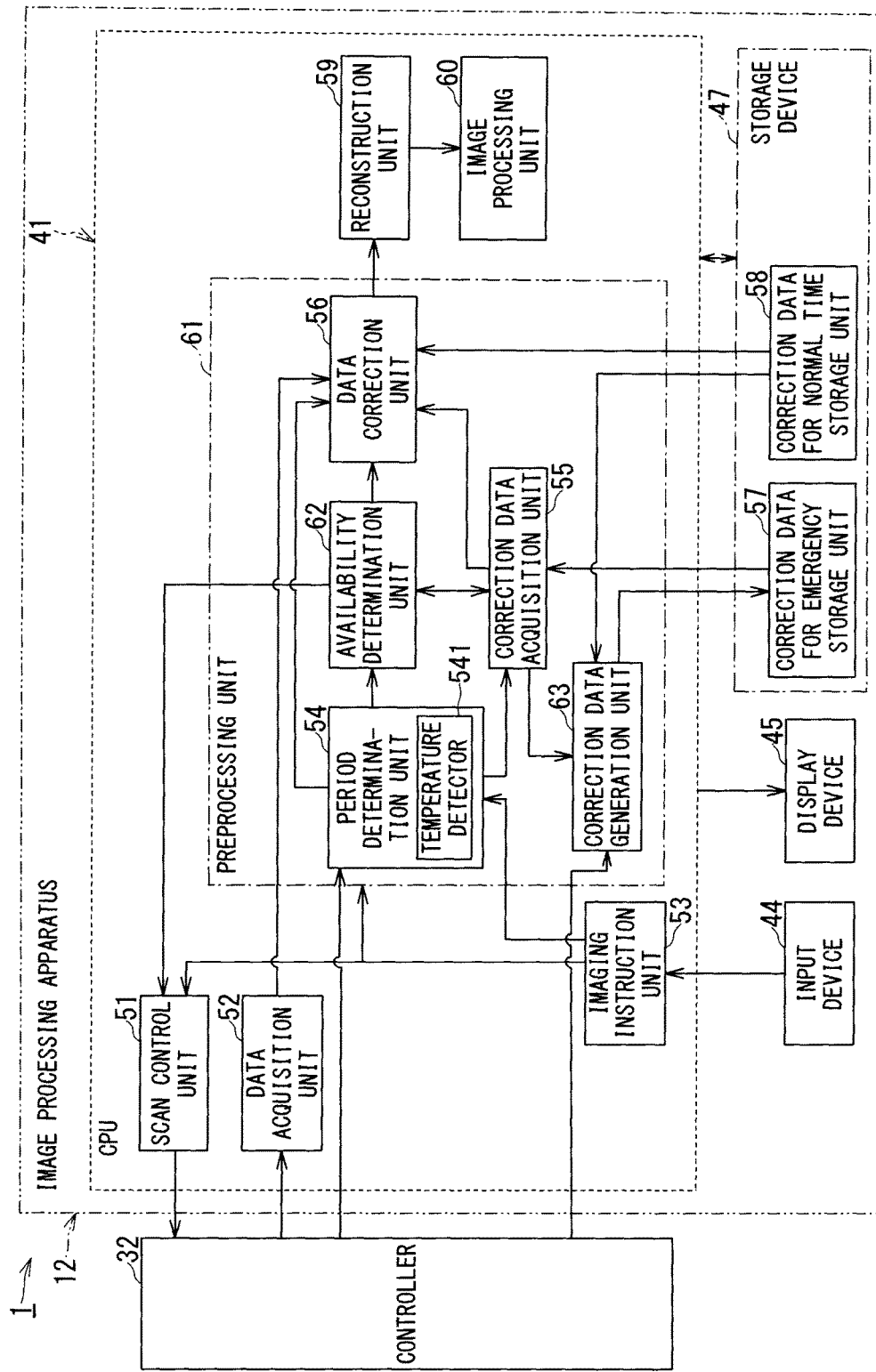
FIG. 2 is a block diagram showing the function of the medical image processing apparatus of the X-ray CT apparatus of the present embodiment.

FIG. 2 is a block diagram showing functions of the image processing apparatus 12 of the X-ray CT apparatus 1 of the present embodiment.

As shown in FIG. 2, the CPU 41 of the image processing apparatus 12 functions as a scan control unit 51, a data acquisition unit 52, an imaging instruction unit 53, a period determination unit 54, a correction data acquisition unit 55, a data correction unit 56, a correction data for emergency storage unit 57, a correction data for normal time storage unit 58, a reconstruction unit 59, and an image processing unit 60, by executing the programs stored in the storage device 47.

In addition, the period determination unit 54, the correction data acquisition unit 55, and the data correction unit 56 constitute a preprocessing unit 61.

In addition, the storage device 47 is a memory area composed of the memory 42, the HDD 43, etc. and constitutes the correction data for emergency storage unit 57 and the correction data for normal time storage unit 58.

Moreover, one or some of the components 51 to 61 of the X-ray CT apparatus 1 may be installed in the X-ray CT apparatus 1 as hardware. In addition, the same reference signs are given for the same components as FIG. 1, and duplicate explanation is omitted.

The scan control unit 51 has a function of performing a scan of the object O by controlling the operation of the scanning apparatus 11 via the controller 32 when the start timing of a scan for generating correction data is detected by the availability determination unit 62 described below. In other words, the scan control unit 51 is configured to perform scan control for generating the correction data described below.

The data acquisition unit 52 obtains output data (radiographic data), which are amplified and then converted into digital signals, from the DAS 24 via the controller 32 of the scanning apparatus 11.

The imaging instruction unit 53 has a function of outputting an instruction to image the object O and acquire radiographic data. Specifically, the imaging instruction unit 53 is configured to acquire an instruction to perform imaging inputted from the input device 44 by a doctor, a clinical examiner or the like, and to give an instruction to image the object O to the scan control unit 51.

The period determination unit 54 is configured to determine whether imaging time of the object O in accordance with the instruction to perform imaging is in a stable period or in an unstable (astable) period, before imaging of the object O. The above stable period (first period) is a period during which the temperature of the X-ray detector 23 is stable, and the above unstable period (second period) is a period during which the temperature of the X-ray detector 23 is not stable.

For example, the period determination unit 54 can determine whether it is in the stable period or in the unstable period, depending on whether or not the temperature information indicating the temperature of the X-ray detector 23 shows a predetermined temperature condition.

Specifically, the X-ray CT apparatus 1 includes a temperature detector 541 which is electrically connected to the period determination unit 54 (this temperature detector 541 generates the temperature information by acquiring the temperature of the X-ray detector 23 from the above-mentioned non-illustrated temperature sensor installed in the X-ray detector 23). The period determination unit 54 can set the predetermined temperature condition so as to determine it as the stable period in the case of the temperature equal to or higher than 40° C. and determine it as the unstable period in the case of the temperature lower than 40° C.

Although the temperature detector 541 is illustrated inside the period determination unit 54 in FIG. 2, this is for the sake of convenience and the temperature detector 541 is actually disposed outside the CPU 41.

As a concrete example, the period determination unit 54 may determine it as the unstable period if the temperature information of the X-ray detector 23 indicates a temperature of 20° C. or higher but lower than 40° C., and determine it as the stable period if the temperature information indicates a temperature of 40° C. or higher but lower than 45° C. This determination algorithm can be achieved by setting a temperature range as the predetermined temperature condition in the period determination unit 54.

Incidentally, when the temperature is equal to or higher than 45° C., the X-ray CT apparatus 1 may output warning to stop imaging because there is a possibility of high temperature abnormality.

The correction data acquisition unit 55 is configured to acquire correction data for emergency from the correction data for emergency storage unit 57, when the imaging time in accordance with the instruction to image the object O is in the unstable period.

The data correction unit 56 corrects the radiographic data obtained from the data acquisition unit 52 by using the acquired correction data for emergency, when the imaging time in accordance with the instruction to image the object O is in the unstable period. On the other hand, the data correction unit 56 is configured to correct the radiographic data obtained from the data acquisition unit 52 by using correction data for normal time preliminarily stored in the correction data for normal time storage unit 58, when the imaging time in accordance with the instruction to image the object O is in the stable period.

The correction data for emergency storage unit 57 is configured to store the correction data for emergency. Incidentally, these correction data for emergency are generated by the correction data generation unit 63 described below.

The correction data for normal time storage unit 58 is configured to store the correction data for normal time which are used for correcting the radiographic data.

The reconstruction unit 59 has a function of reconstructing X-ray CT images by using the corrected radiographic data. Incidentally, in the present embodiment, the data correction unit 56 is configured to perform various types of correction processing (for example, correction processing such as logarithmic transformation processing, sensitivity correction processing, etc.) on the radiographic data. Additionally, in the present embodiment, the reconstruction unit 59 is configured to perform reconstruction processing on the corrected radiographic data (these data are also referred to as projection data) by using known inverse projection processing or the like.

The image processing unit 60 generates display image data by performing image processing on the reconstructed radiographic data (i.e. projection data). The image processing unit 60 stores the generated display image data in the storage device 47 composed of the memory 42, the HDD 43 and so on.

The above-mentioned preprocessing unit 61 is configured to include the period determination unit 54, the correction data acquisition unit 55, and the data correction unit 56. Therefore, the preprocessing unit 61 determines whether the imaging time in accordance with the instruction to image the object O is in the stable period during which the temperature of the X-ray detector 23 is stable or in the unstable period during which the temperature of the X-ray detector 23 is not stable, before the imaging of the object O.

When the imaging time of the object O is in the unstable period, the preprocessing unit 61 acquires the correction data for emergency and corrects the radiographic data generated by the imaging with the use of the acquired correction data for emergency. On the other hand, when the imaging time of the object O is in the stable period, the preprocessing unit 61 is configured to correct the radiographic data generated by the imaging with the use of the preliminarily stored correction data for normal time.

In addition, the preprocessing unit 61 may further include an availability determination unit 62 and a correction data generation unit 63 as its arbitrary components.

The availability determination unit 62 is configured to determine whether the correction data for emergency acquired from the correction data for emergency storage unit 57 by the correction data acquisition unit 55 is available or not (valid or invalid). Thus, when the correction data for emergency is determined to be unavailable, the correction data acquisition unit 55 is configured to reacquire (regenerate) the correction data for emergency at this determination timing.

As an example of regenerating the correction data for emergency at this determination timing, in the present embodiment, the correction data generation unit 63 has a function of generating the correction data for emergency at imaging time of the object O. In other words, the correction data generation unit 63 generates intended correction data for emergency, and thereby the correction data acquisition unit 55 is configured to be able to acquire the correction data for emergency.

Here, an example in which the correction data generation unit 63 generates correction data for emergency will be explained.

First, when imaging of the object O is performed in an emergency, the following two cases are included. One of them is a case where the imaging conditions of this object O are stored in the correction data for emergency storage unit 57 and, the other is a case where they are not stored. When the imaging conditions of this object O are stored, it is enough to use the stored imaging conditions. On the other hand, when the imaging conditions of this object O are not stored, it is assumed that the imaging conditions of this object O are inputted via the input device 44.

As the imaging conditions for imaging of the object O, for example, a doctor inputs a tube voltage (kV), a combination of slice thickness (mm) and number of columns, an imaging region, a gain, an imaging mode, etc. As the imaging region, there are the head, the trunk part, etc. and the imaging region is selected in accordance with the object O. As the gain, a plurality of gains such as one time, three times, five times, ten times, twenty times, etc. are prepared.

An imaging region and a gain generally correspond to each other in one-to-one relation. Thus, if a certain imaging region is selected, its gain is uniquely determined. Incidentally, the relationship between an imaging region and a gain can be defined in a way different from the above one-to-one relationship, and a plurality of gains are prepared in a certain imaging region in some cases.

The correction data for normal time are based on the radiographic data obtained by imaging a phantom (hereinafter, these are referred to as phantom data), and are obtained by performing image quality improving processing such as ring artifact removing processing etc. on the phantom data. Here, a phantom is a water bag, resin whose internal density is uniform, or the like. A phantom with a specific size is used for each imaging part of the object O such as the head, the trunk, etc. Thus, the phantom data are data on which change in sensitivity characteristics is reflected.

In addition, as to the correction data for emergency generated by the correction data generation unit 63, the correction data for normal time optimum for the imaging conditions and the channel are read out from the correction data for normal time storage unit 58, and the correction data for emergency are generated based on these optimum correction data for normal time before the main scan is executed by the scanning apparatus 11. Therefore, the correction data generation unit 63 performs calculation under the following formula (1).

radiographic data after correction $Tc(Cy,CHz)$=radiographic data $Tb(Cy,CHz)$/correction data($Cy$, $CHz$)  (1)

Incidentally, Cy indicates predetermined imaging conditions, CHz indicates a predetermined channel. In addition, the radiographic data after correction are assumed to be projection data.

The correction data generation unit 63 corrects the correction data for normal time so as to reflect sensitivity characteristics at the time of performing correction for emergency, and stores the corrected correction data for normal time in the correction data for emergency storage unit 57, for example. In such processing of correcting correction data, the radiographic data of air at both times for normal time and emergency (hereinafter, the respective radiographic data are referred to as air data) are acquired, and change in sensitivity characteristics of the air data from the time of generating correction data for normal time to the time of generating correction data for emergency are calculated. Then, the phantom data of correction data for normal time (hereinafter, these are referred to as reference phantom data) are subjected to such processing as to reflect the change in sensitivity characteristics, and the phantom data at the time of performing correction for emergency (phantom data for emergency) are generated.

Specifically, by computing the following formula (2), correction data for emergency at the time of emergency can be generated.

correction data for emergency=$Ws(Gx,Cy)*\{An(Gx,Cy)/As(Gx,Cy)\}$  (2)

Incidentally, Ws(Gx, Cy) indicates the reference phantom data under the imaging conditions Cy and the gain Gx, and the correction data for normal time are generated by performing image quality improving processing such as ring artifact removing processing etc. on the reference phantom data. In addition, An(Gx, Cy) indicates the air data (air data for emergency) at the time of generating the correction data for emergency under the imaging conditions Cy and the gain Gx. In addition, As(Gx, Cy) indicates air data (air data for normal time) of the reference time under the imaging conditions Cy and the gain Gx.

When the correction data generation unit 63 generates the correction data for emergency, (a) an X-ray beam is irradiated on air under imaging conditions for a unified imaging region, (b) the detected X-ray beam is amplified by the gain, (c) the air data for emergency An(Gx, Cy) are acquired, and (d) the correction data for emergency are generated by using the formula (2).

Incidentally, the above-mentioned method of generating the correction data for emergency is only an example, and the correction data for emergency may be generated by using other methods.

For example, the correction data generation unit 63 can generate phantom data by imaging a phantom in the unstable period during which imaging is to be performed and treat the generated phantom data as the correction data for emergency (Wn). Then, the correction data generation unit 63 is configured to store the generated correction data for emergency in the correction data for emergency storage unit 57, as soon as it generates the correction data for emergency.

(Image Data Generation Processing for Emergency)

Next, operation of image data generation processing for emergency performed by the image processing apparatus 12 of the X-ray CT apparatus 1 of the present embodiment will be explained.

Figure 3:
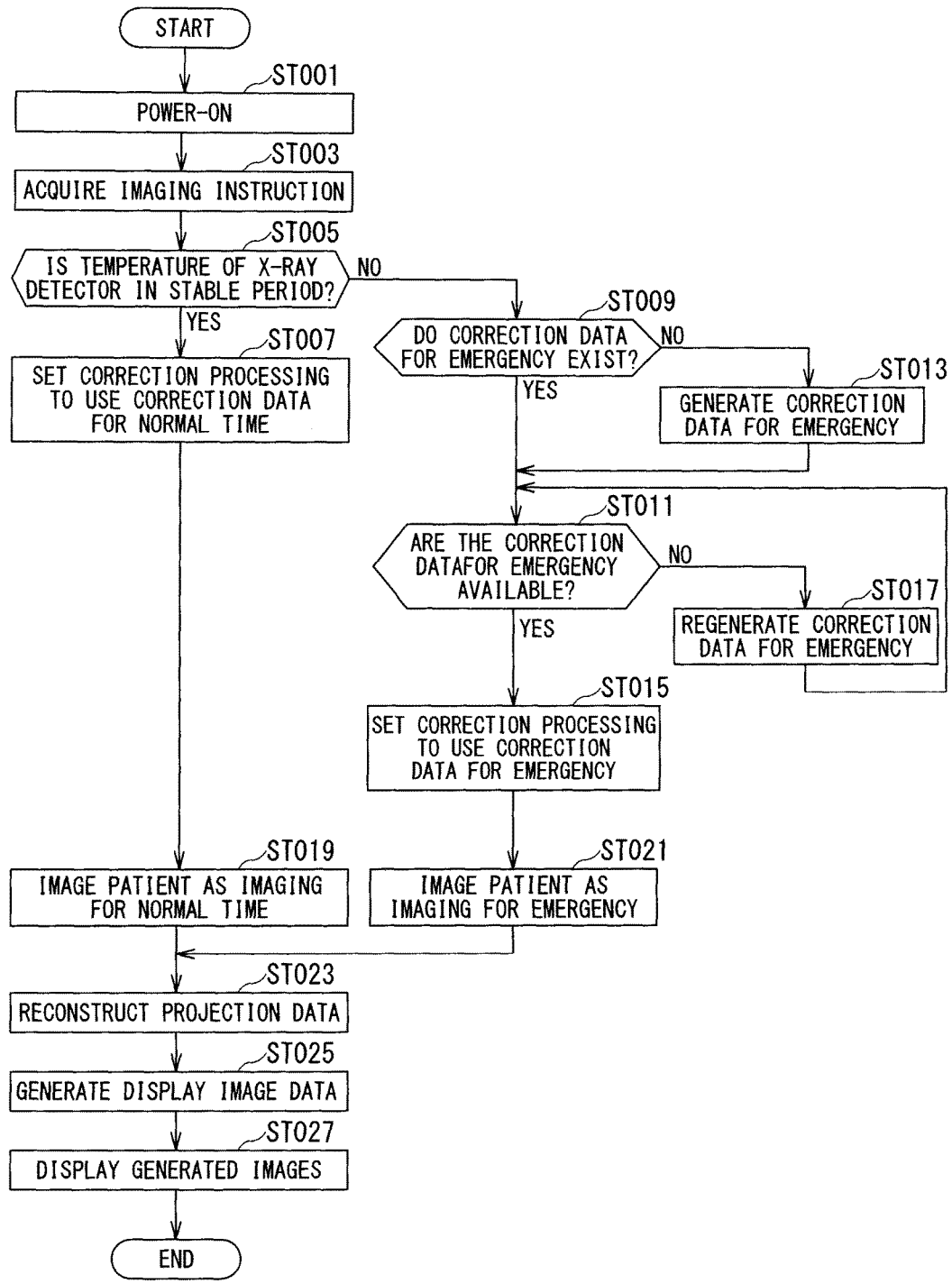
FIG. 3 is a flowchart showing image data generation processing for emergency, in which the image processing device of the X-ray CT apparatus of the present embodiment determines whether the temperature of the X-ray detector is stable or not and generates correction data for emergency so as to generate image data even in an unstable period of the temperature of the X-ray detector.

FIG. 3 is a flowchart showing the image data generation processing for emergency, in which the image processing apparatus 12 of the X-ray CT apparatus 1 of the present embodiment determines whether the temperature of the X-ray detector 23 is stable or not and generates the correction data for emergency so as to generate image data even in the unstable period during which the temperature is not stable. Incidentally, in FIG. 3, the reference numbers added next to ST indicate the respective steps of the flowchart.

First, in the step ST001, power is supplied to the scanning apparatus 11 of the X-ray CT apparatus 1, and energization of the X-ray detector 23 is started. Incidentally, the energization of the X-ray detector 23 is not limited to power supply from the scanning apparatus 11 but the image processing apparatus 12 may be configured to be able to power on the X-ray detector 23.

Next, in the step ST003, the image processing apparatus acquires an instruction (command) to perform imaging, which is inputted by a doctor or a clinical examiner via the input device 44, in the imaging instruction unit 53. Then, the imaging instruction unit 53 gives an instruction to image the object O to the scan control unit 51.

In the step ST005, the period determination unit 54 of the image processing apparatus 12 determines whether the imaging time in accordance with the imaging instruction is in the stable period during which the temperature of the X-ray detector 23 is stable or in the unstable period during which the temperature of the X-ray detector 23 is not stable, before the imaging of the object O.

For example, the period determination unit 54 can determine whether the imaging time is in the stable period or in the unstable period, depending on whether or not the temperature information indicating the temperature of the X-ray detector 23 shows a predetermined temperature condition. Specifically, the period determination unit 54 can set the predetermined temperature condition so as to determine it as the stable period in the case of the temperature of the X-ray detector 23 indicated by the temperature information is equal to or higher than 400° C. and determine it as the unstable period in the case of the temperature lower than 400° C.

In addition, the period determination unit 54 may set the predetermined temperature condition so as to determine whether it is in the stable period or in the unstable period, based on temperature change rate indicating temperature change of the X-ray detector 23. For example, the period determination unit 54 may stipulate the temperature change rate of the temperature of the X-ray detector 23 based on the past statistics so as to determine whether it is in the stable period or in the unstable period, in accordance with the stipulated value of the temperature change rate. This is because the temperature change of the X-ray detector 23 varies depending on a season and a time zone.

In addition, the period determination unit 54 may start energization of the X-ray detector 23 and determine whether it is in the stable period or in the unstable period, on the basis of the elapsed time after starting the energization of the X-ray detector. For example, the period determination unit 54 may determine it to be in the stable period if two hours have already elapsed after starting the energization of the X-ray detector, and may determine it to be in the unstable period if two hours have not elapsed yet from the start of the energization.

The step ST007 corresponds to the case where the period determination unit 54 has determined that the imaging time in accordance with the instruction to image the object O is in the stable period during which the temperature of the X-ray detector 23 is stable (corresponding to YES in the step ST005). In the step ST007, the period determination unit 54 sets the data correction unit 56 to correct the radiographic data acquired from the data acquisition unit 52 by using the correction data for normal time preliminarily stored in the correction data for normal time storage unit 58.

On the other hand, when the imaging time in accordance with the instruction to image the object O is determined to be in the unstable period (corresponding to NO in the step ST005), the period determination unit 54 determines whether the correction data for emergency exists in the correction data for emergency storage unit 57 or not, by using the correction data acquisition unit 55 (in the step ST009).

When the correction data for emergency exists in the correction data for emergency storage unit 57 in the step ST009 (corresponding to YES in the step ST009), the correction data acquisition unit 55 acquires the correction data for emergency stored in the correction data for emergency storage unit 57, and the availability determination unit 62 determines whether the acquired correction data for emergency are available or not (in the step ST011).

On the other hand, the correction data for emergency do not exist in the correction data for emergency storage unit 57 (corresponding to NO in the step ST009), the availability determination unit 62 gives an instruction to perform a scan for generating the correction data for emergency to the scan control unit 51, and makes the correction data generation unit 63 generate the correction data for emergency corresponding to the current temperature of the X-ray detector 23 (in the step ST013). In this case, the correction data generation unit 63 generates the correction data for emergency by calculating the air data for emergency and the phantom data for emergency. Then, the correction data generation unit 63 stores the generated correction data for emergency in the correction data for emergency storage unit 57.

As just described, the availability determination unit 62 makes the correction data generation unit 63 generates the correction data for emergency on the basis of various radiographic data obtained via the controller 32, by making the scanning apparatus 11 perform the scan for generating the correction data for emergency just before imaging.

In the step ST011, the availability determination unit determines whether the correction data for emergency acquired from the correction data acquisition unit 55 are available or not. When the correction data for emergency are determined to be available (corresponding to YES in the step ST011), the data correction unit 56 reads out the correction data for emergency from the correction data acquisition unit and sets the radiographic data acquired from the data acquisition unit 52 to be subjected to correction with the use of the correction data for emergency (in the step ST015).

On the other hand, when the correction data for emergency are determined to be unavailable (corresponding to NO in the step ST011), the availability determination unit 62 makes the correction data generation unit 63 regenerate the correction data for emergency corresponding to the current temperature of the X-ray detector 23 via the scan control unit 51 (in the step ST017). In this case, the correction data generation unit 63 generates the correction data for emergency again by calculating the air data for emergency and the phantom data for emergency, and stores the regenerated correction data for emergency in the correction data for emergency storage unit 57.

Incidentally, as to methods of regenerating the correction data for emergency, the same method as the generation method of the correction data in the step ST013 can be used.

In addition, when the availability determination unit determines availability of the correction data for emergency in the step ST011, the availability determination unit 62 can determine the availability based on elapsed time from acquisition of the correction data for emergency by the correction data acquisition unit 55 to the timing when the radiographic data are to be corrected, as an example. In this case, for example, 30 minutes can be set as the elapsed time.

Moreover, by reflecting the elapsed time from starting the energization of the X-ray detector 23 in addition to the elapsed time from acquiring the correction data for emergency to the actual timing of imaging the object O, the availability determination unit 62 may determine the availability of the correction data for emergency based on (a) the elapsed time from starting the energization of the X-ray detector 23 and (b) the elapsed time until actually imaging is performed.

In addition, by reflecting the temperature information indicating the temperature of the X-ray detector 23 in addition to the elapsed time from acquiring the correction data for emergency to the actual timing of imaging the object O, the availability determination unit 62 may determine the availability of the correction data for emergency based on (a) the temperature information indicating the temperature of the X-ray detector 23 and (b) the elapsed time until actually imaging is performed.

When the correction data for emergency are regenerated in the step ST017, the availability determination unit 62 determines whether the correction data for emergency is available or not again, based on the regenerated correction data for emergency (in the step ST011). Then, the availability determination unit 62 sets the data correction unit 56 to correct the radiographic data acquired from the data acquisition unit 52 by using the correction data for emergency determined to be available (in the step ST015).

Next, the scanning apparatus 11 of the X-ray CT apparatus 1 images the object O by performing a main scan on the basis of instructions inputted by an operator such as a doctor and so on. Specifically, when the image processing apparatus 12 is set to perform correction processing by using the correction data for normal time (in the step ST007), the X-ray CT apparatus 1 images a patient as imaging for normal time (in the step ST019).

On the other hand, when the image processing apparatus is set to perform correction processing by using the correction data for emergency (in the step ST021), the scanning apparatus 11 of the X-ray CT apparatus 1 similarly images the object O by performing the main scan based on instructions inputted by an operator such as a doctor etc. However, because the image processing apparatus 12 is set to perform correction processing by using the correction data for emergency (in the step ST015), the X-ray CT apparatus 1 images a patient as imaging for emergency (in the step ST021).

Incidentally, in the present embodiment, the image processing apparatus 12 is alternatively selected to perform correction processing by using the correction data for normal time or to perform correction processing by using correction data for emergency, depending on whether the temperature of the X-ray detector 23 is in the stable period or in the unstable period. The data acquisition unit 52 acquires the radiographic data generated by the scanning apparatus 11 via the controller 32, and the data correction unit 56 corrects the radiographic data obtained from the data acquisition unit 52 by using either of the correction data for normal time or the correction data for emergency (in the step ST019 or the step ST021).

In the step ST023, the reconstruction unit 59 performs reconstruction of the corrected radiographic data (i.e. the projection data). The reconstruction unit 59 performs reconstruction processing on the projection data generated by the data correction unit 56, with the use of known inverse projection processing technique etc.

In the step ST025, the image processing unit 60 performs image processing on the reconstructed projection data so as to generate display image data. The image processing unit 60 stores the generated display image data in the storage device 47.

In the step ST027, the CPU 41 makes the display device 45 display the generated display image data.

As mentioned above, according to the X-ray CT apparatus 1 of the present embodiment, the period determination unit 54 of the image processing apparatus 12 determines whether the imaging time in accordance with the instruction to image the object O is in the stable period during which the temperature the X-ray detector 23 is stable or in the unstable period during which the temperature is not stable, before the imaging of the object O. Then, even if the imaging time in accordance with the instruction to image the object O is in the unstable period during which the temperature is not stable, the correction data acquisition unit 55 acquires the correction data for emergency stored in the correction data for emergency storage unit 57 and the data correction unit 56 can correct the radiographic data acquired from the data acquisition unit 52 by using the correction data for emergency.

Thereby, the X-ray CT apparatus 1 of the present embodiment can appropriately correct the radiographic data generated by imaging according to the stability of the X-ray detector 23, even under the state where the temperature of the X-ray detector 23 is not stable.

Incidentally, the CPU 41 is an example of the processing circuitry described in the claims, and the storage device 47 is an example of the storage circuit described in the claims. In addition, the DAS 24 is an example of the acquisition circuit described in the claim. Note that the above correspondences are just some of possible interpretations for reference and should not be construed as limiting embodiments of the present disclosure.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

In addition, in the embodiment of the present invention, an example in which each step of the flowchart (FIG. 3) is time-sequentially performed in the described order has been explained. However, each step of the flowchart does not necessarily need to be time-sequentially performed. Embodiments of the present invention also include aspects in which the respective steps of the flowchart are performed in parallel or individually.

What is claimed is:

1. A medical image processing apparatus comprising:
    a storage circuit configured to store first correction data and/or second correction data; and
    processing circuitry configured to
        generate the first correction data based on an imaging during a first period when a temperature of an X-ray detector is stable,
        generate the second correction data during a second period when the temperature of the X-ray detector is not stable, the second correction data being generated by calculating a change of sensitivity between air data acquired during the first period and air data acquired during the second period and applying the change of sensitivity to the first correction data,
        output a command to perform imaging of an object and acquire radiographic data,
        determine whether imaging time of the object is during the first period or the second period, and
        correct the radiographic data by using the second correction data when the imaging time of the object is during the second period, and correct the radiographic data by using the first correction data when the imaging time of the object is during the first period.

2. The medical image processing apparatus according to claim 1, wherein the processing circuitry is configured to generate the second correction data and record the second correction data on the storage circuit when the imaging time of the object is during the second period.

3. The medical image processing apparatus according to claim 2, wherein the processing circuitry is configured to
    acquire temperature information indicating temperature of the X-ray detector,
    determine whether the imaging time is during the first period or the second period, based on the temperature information, and
    generate the second correction data when the imaging time of the object is during the second period.

4. The medical image processing apparatus according to claim 2, wherein the processing circuitry is configured to
    determine whether the imaging time of the object is during the first period or the second period, based on temperature change rate indicating temperature change of the X-ray detector, and generate the second correction data when the imaging time of the object is during the second period.

5. The medical image processing apparatus according to claim 2, wherein the processing circuitry is configured to
acquire information on elapsed time after start of power supply to the X-ray detector,
determine whether the imaging time of the object is during the first period or the second period, based on the information on elapsed time, and
generate the second correction data when the imaging time of the object is during the second period.

6. The medical image processing apparatus according to claim 2, wherein the processing circuitry is configured to
perform determination as to whether past second correction data of the second correction data are available or not,
generate new second correction data of the second correction data at a time of the determination, when the past second correction data are determined to be unavailable, and
correct the radiographic data by using the new second correction data.

7. The medical image processing apparatus according to claim 6, wherein the processing circuitry is configured to
perform determination as to whether the past second correction data are available or not, based on elapsed time from generation timing of the past second correction data to actual imaging of the object,
generate the new second correction data at a time of the determination, when the past second correction data are determined to be unavailable, and
correct the radiographic data by using the new second correction data.

8. The medical image processing apparatus according to claim 6, wherein the processing circuitry is configured to
perform determination as to whether the past second correction data are available or not, based on first elapsed time from generation timing of the past second correction data to actual imaging of the object and second elapsed time after start of power supply to the X-ray detector,
generate the new second correction data at a time of the determination, when the past second correction data are determined to be unavailable, and
correct the radiographic data by using the new second correction data.

9. The medical image processing apparatus according to claim 6, wherein the processing circuitry is configured to
perform determination as to whether the past second correction data are available or not, based on elapsed time from generation timing of the past second correction data to actual imaging of the object and temperature information indicating temperature of the X-ray detector,
generate the new second correction data at a time of the determination, when the past second correction data are determined to be unavailable, and
correct the radiographic data by using the new second correction data.

10. An X-ray CT apparatus comprising:
an X-ray source configured to irradiate X-rays;
an X-ray detector configured to detect the X-rays;
a data acquisition circuit configured to acquire radiographic data of X-rays detected by the X-ray detector;
a storage circuit configured to store first correction data and/or second correction data; and
processing circuitry configured to
generate the first correction data based on an imaging during a first period when a temperature of an X-ray detector is stable,
generate the second correction data during a second period when the temperature of the X-ray detector is not stable, the second correction data being generated by calculating change of sensitivity between air data acquired during the first period and air data acquired during the second period and applying the change of sensitivity to the first correction data,
output a command to acquire radiographic data by performing imaging of an object using the X-ray source, the X-ray detector, and the data acquisition circuit,
determine whether imaging time of the object is during the first period or the second period,
correct the radiographic data by using the second correction data when the imaging time of the object is during the second period, and correct the radiographic data by using the first correction data when the imaging time of the object is during the first period, and
reconstruct an X-ray CT image by using corrected radiographic data.

* * * * *